US008292816B2

(12) United States Patent
Yoshimura (10) Patent No.: US 8,292,816 B2
(45) Date of Patent: Oct. 23, 2012

(54) ULTRASONIC IMAGE DIAGNOSTIC APPARATUS (75) Inventor: Takehiro Yoshimura, Akishima (JP)

(73) Assignee: Olympus Corporation, Tokyo (JP)

( * ) Notice: Subject to any disclaimer, the term of this patent is extended or adjusted under 35 U.S.C. 154(b) by 1096 days.

(21) Appl. No.: 11/602,533

(22) Filed: Nov. 21, 2006

(65) Prior Publication Data
US 2007/0167796 A1 Jul. 19, 2007

Related U.S. Application Data (63) Continuation of application No. PCT/JP2005/009342, filed on May 23, 2005.

(30) Foreign Application Priority Data

May 24, 2004 (JP) ................................. 2004-153953

(51) Int. Cl.
A61B 8/00 (2006.01)

(52) U.S. Cl. ........................................................ 600/443

(58) Field of Classification Search ................... 600/443
See application file for complete search history.

(56) References Cited

U.S. PATENT DOCUMENTS

2001/0016686 A1* 8/2001 Okada et al. ................... 600/454
2003/0236462 A1* 12/2003 Salgo et al. ................... 600/443

FOREIGN PATENT DOCUMENTS

| JP | 06-203158 | | 7/1994 |
| JP | 07-334702 | | 12/1995 |
| JP | 2000-296129 | | 10/2000 |
| JP | 2001-178725 | | 7/2001 |
| JP | 2003-265475 | | 9/2003 |
| JP | 2003265475 A | * | 9/2003 |

* cited by examiner

Primary Examiner — Brian Casler
Assistant Examiner — Saurel J Selkin
(74) Attorney, Agent, or Firm — Scully, Scott, Murphy & Presser, P.C.

(57) ABSTRACT

An image processor includes a signal processing circuit for performing signal processing on three-dimensional echo signals transmitted from an ultrasonic 3D probe, a memory for storing at least one set of plural sets of three-dimensional echo data converted by the signal processing circuit, a large capacity storage unit, a control circuit for controlling input/output signals from an input unit, an image processing circuit for performing image processing such as coordinate conversion based on the three-dimensional echo data stored in the memory, a display circuit for displaying the ultrasonic three-dimensional image processed by the image processing circuit, and a CPU for performing calculation for "volume measurement". Accordingly, a tissue of interest can be easily and accurately measured.

2 Claims, 9 Drawing Sheets

RADIAL CROSS-SECTION

LINEAR CROSS-SECTION

FIG.13

RADIAL CROSS-SECTION

LINEAR CROSS-SECTION

FIG.14

RADIAL CROSS-SECTION

LINEAR CROSS-SECTION

FIG.15

RADIAL CROSS-SECTION

LINEAR CROSS-SECTION

ULTRASONIC IMAGE DIAGNOSTIC APPARATUS

CROSS REFERENCE TO RELATED APPLICATION

This application is a continuation application of PCT/JP 2005/009342 filed on May 23, 2005 and claims benefit of Japanese Application No. 2004-153953 filed in Japan on May 24, 2004, the entire contents of which are incorporated herein by this reference.

BACKGROUND OF THE INVENTION

1. Field of the Invention

The present invention relates to ultrasonic image diagnostic apparatuses that perform three-dimensional ultrasonic scanning on a subject to observe and examine the subjects.

2. Description of the Related Art

Heretofore, there have been used ultrasonic image diagnostic apparatuses that perform diagnoses based on ultrasonic images of living organs by inserting an ultrasonic probe, provided with an ultrasonic search unit in a tip end thereof, into a body cavity, and by transmitting or receiving ultrasonic waves to or from the living organs by using the ultrasonic search unit.

One of the living organs to be diagnosed may be the prostate, and the diagnosis of the prostate requires not only the shape of the prostate, but also the volume thereof, as important diagnostic factors.

Therefore, as described in Japanese Unexamined Patent Application Publication No. 2001-178725, a method is employed that the volume of a spheroid is calculated based on two axes orthogonal to each other assigned in an ultrasonic topographic image.

SUMMARY OF THE INVENTION

An ultrasonic image diagnostic apparatus according to an aspect of the present invention can perform three-dimensional ultrasonic scanning on a subject, and display an arbitrary first tomographic image of the subject and a second tomographic image perpendicular to the first tomographic image, by using ultrasonic data in a three-dimensional region obtained according to the ultrasonic scanning. The ultrasonic image diagnostic apparatus includes: measurement line setting means for setting segments to be measured, for two systems applied to the first tomographic image, and for one system applied to the second tomographic image; measurement means for performing volume measurement based on the segments set by the measurement line setting means; and display means for displaying a measurement result and a measurement range obtained by the measurement means.

DESCRIPTION OF THE PREFERRED EMBODIMENTS

An embodiment of the present invention will be described below with reference to the attached drawings.

(First Embodiment)

Figure 1:
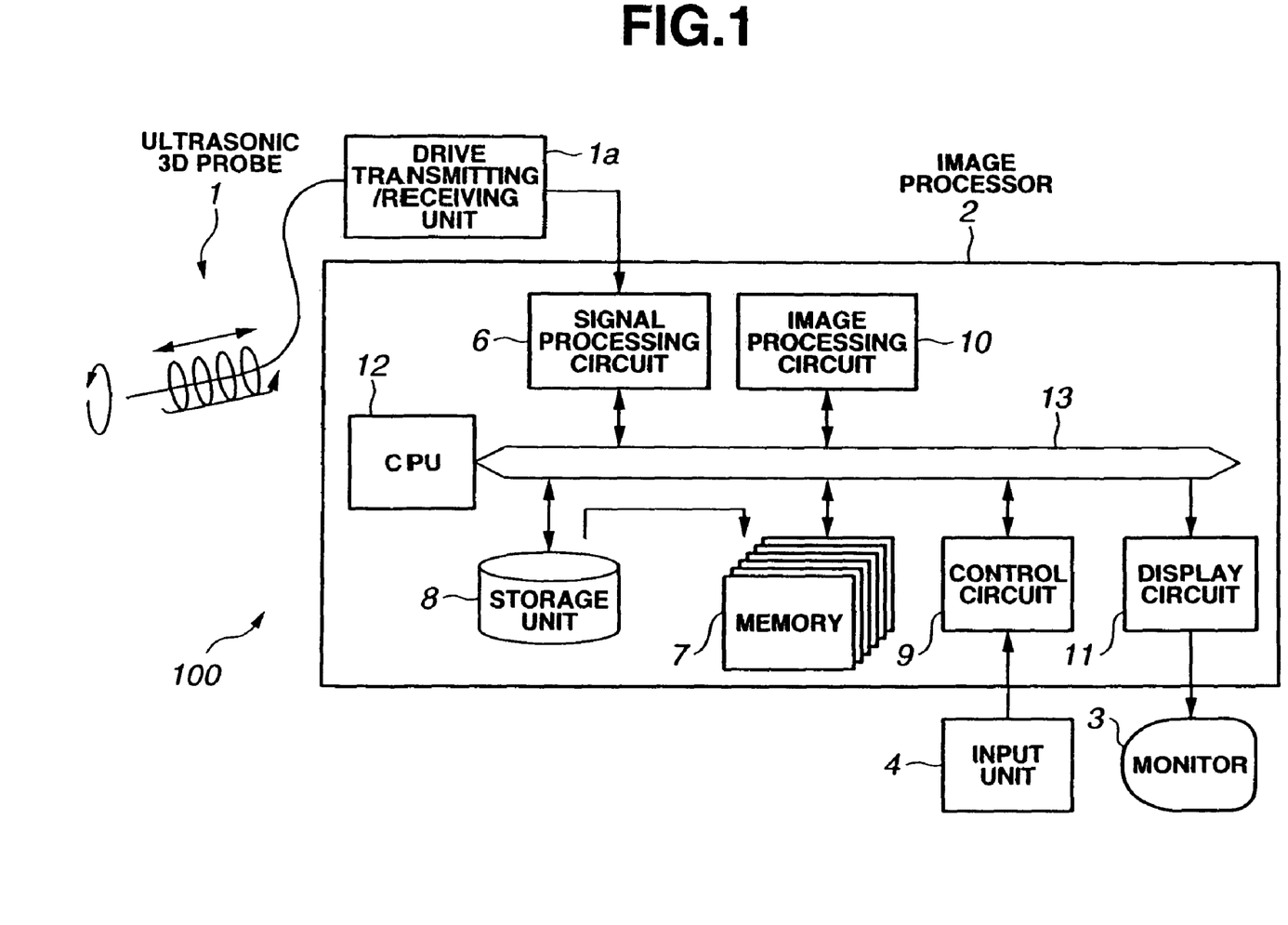
FIG. 1 is a block diagram showing an ultrasonic image diagnostic apparatus according to a first embodiment of the present invention.
Figure 2:
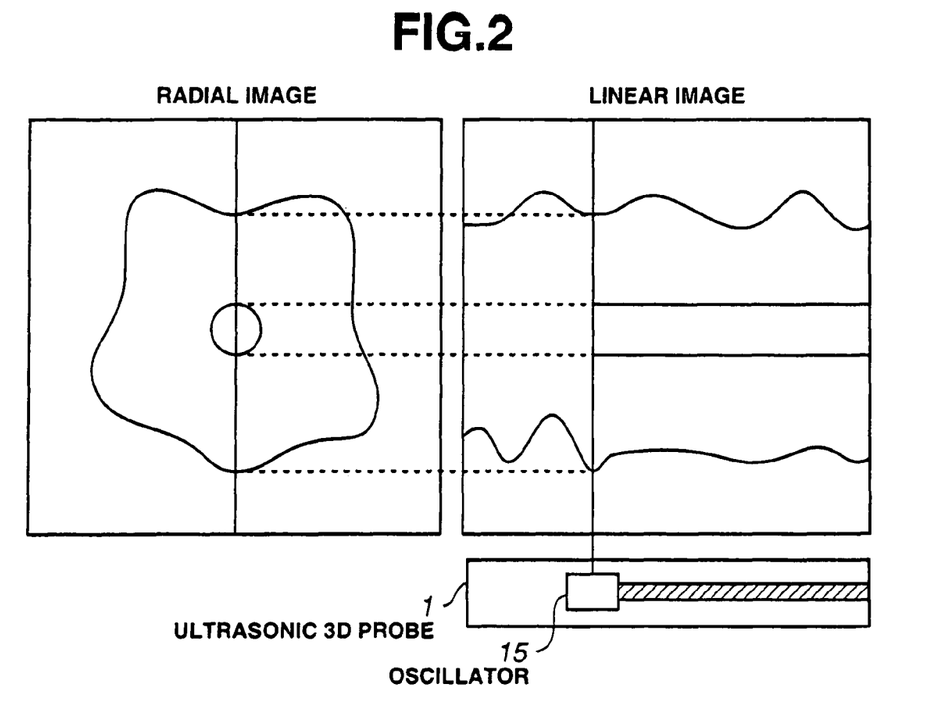
FIG. 2 is an illustration showing images (images in which a radial cross-section and a linear cross-section are developed) which are processed by an image processing circuit based on three-dimensional echo data stored in a memory shown in FIG. 1.
Figure 3:
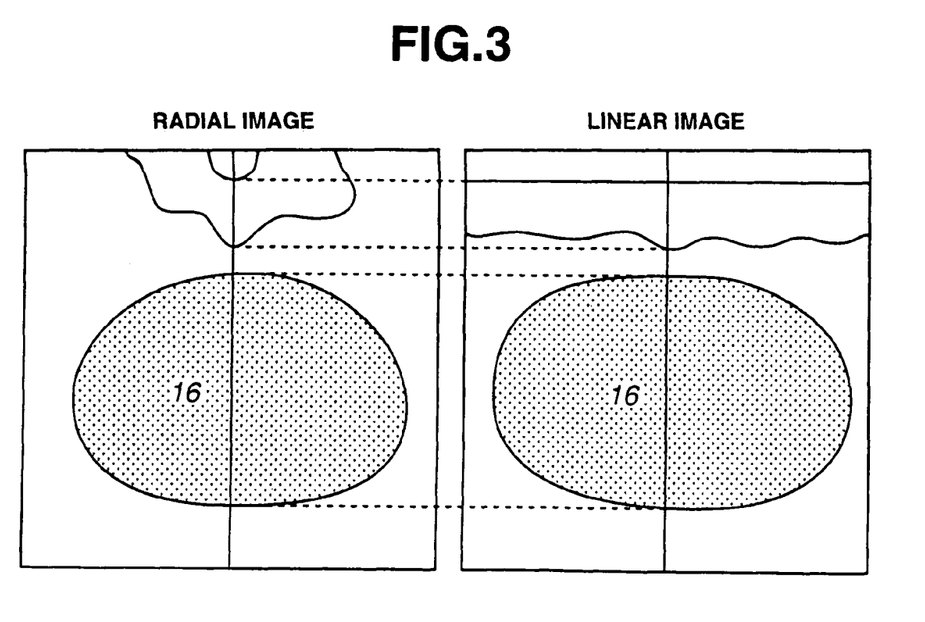
FIG. 3 is an illustration showing a specific tissue (for instance, the prostate) in a lower semicircle display (display showing only the lower half from the center) of the radial cross-section shown in FIG. 2.
Figure 4:
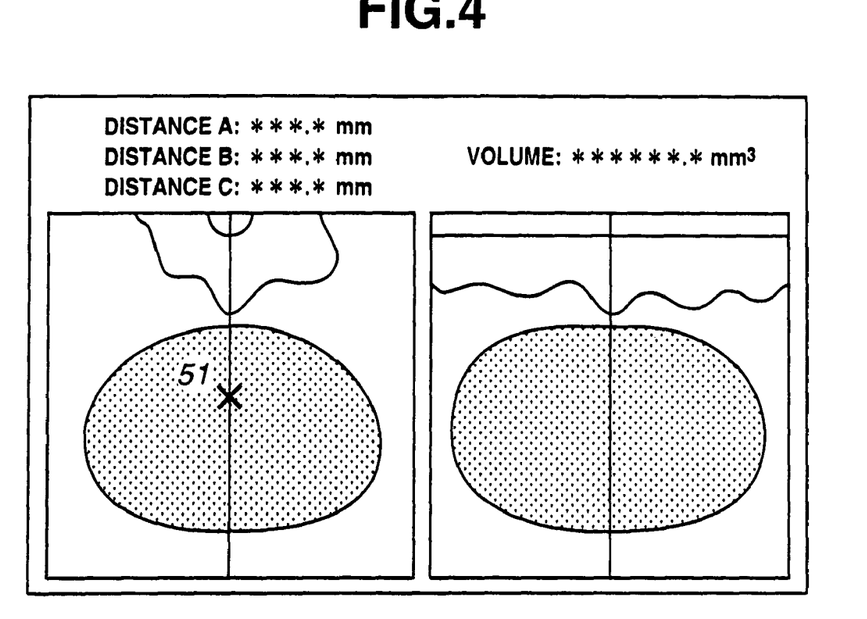
FIG. 4 is a first illustration showing a step for measuring the volume of the specific tissue shown in FIG. 3.
Figure 5:
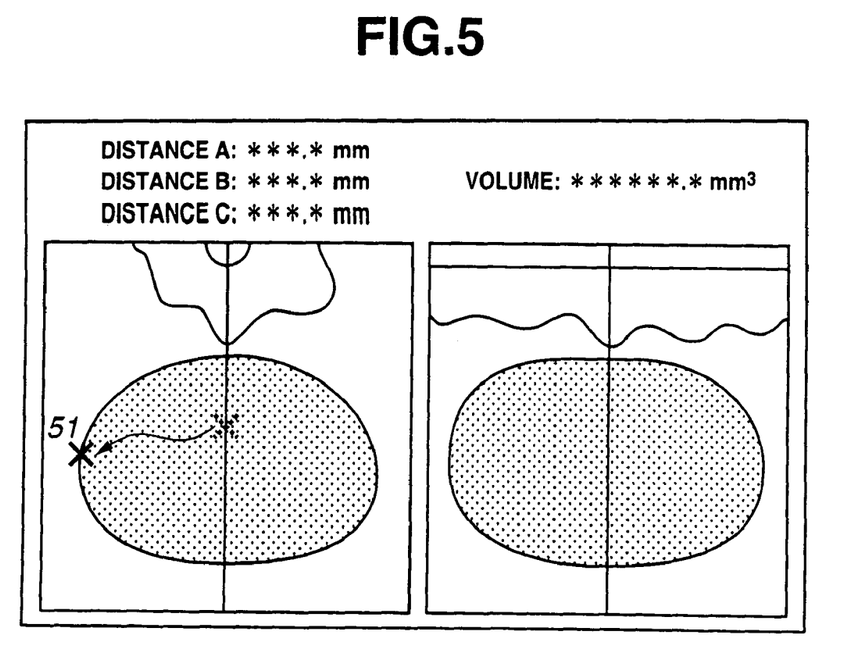
FIG. 5 is a second illustration showing a step for measuring the volume of the specific tissue shown in FIG. 3.
Figure 6:
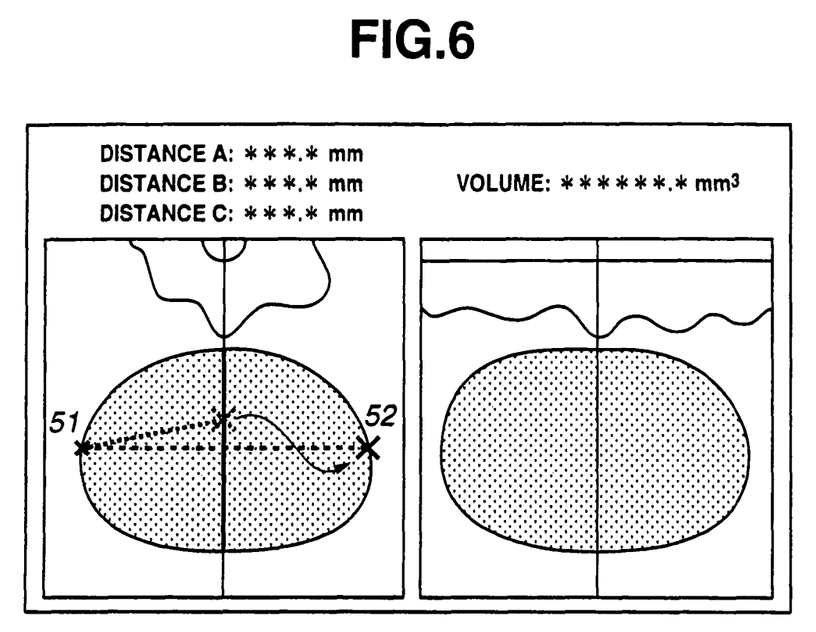
FIG. 6 is a third illustration showing a step for measuring the volume of the specific tissue shown in FIG. 3.
Figure 7:
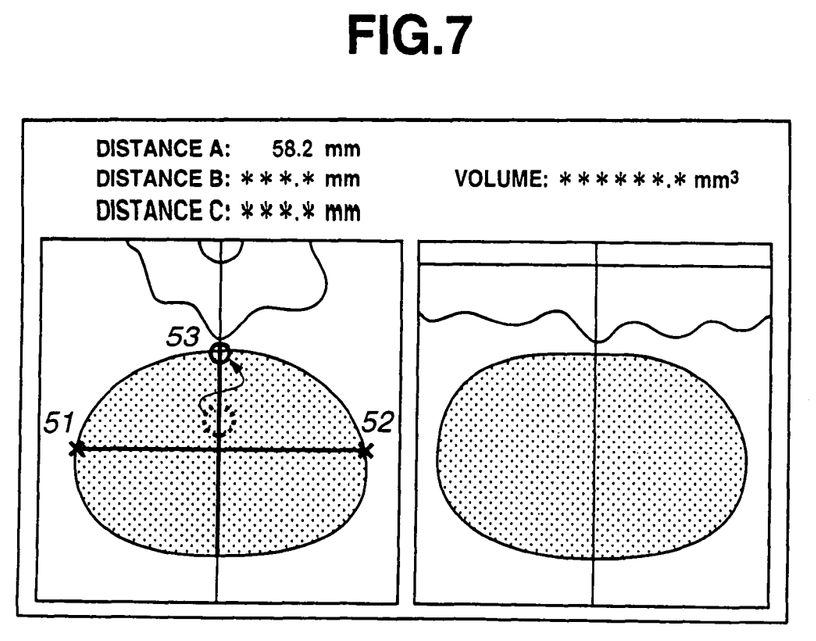
FIG. 7 is a fourth illustration showing a step for measuring the volume of the specific tissue shown in FIG. 3.
Figure 8:
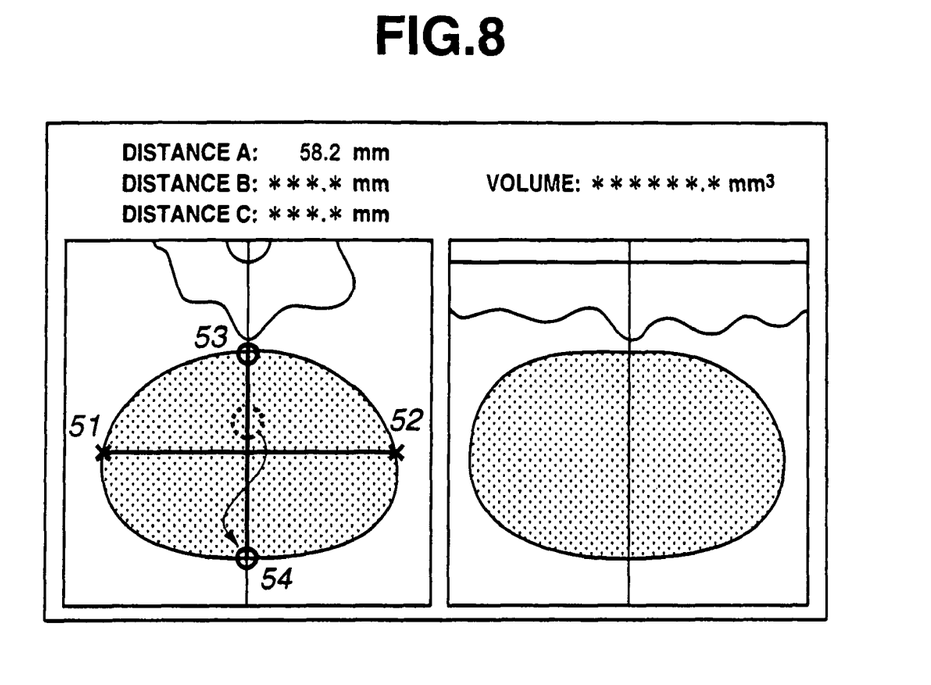
FIG. 8 is a fifth illustration showing a step for measuring the volume of the specific tissue shown in FIG. 3.
Figure 9:
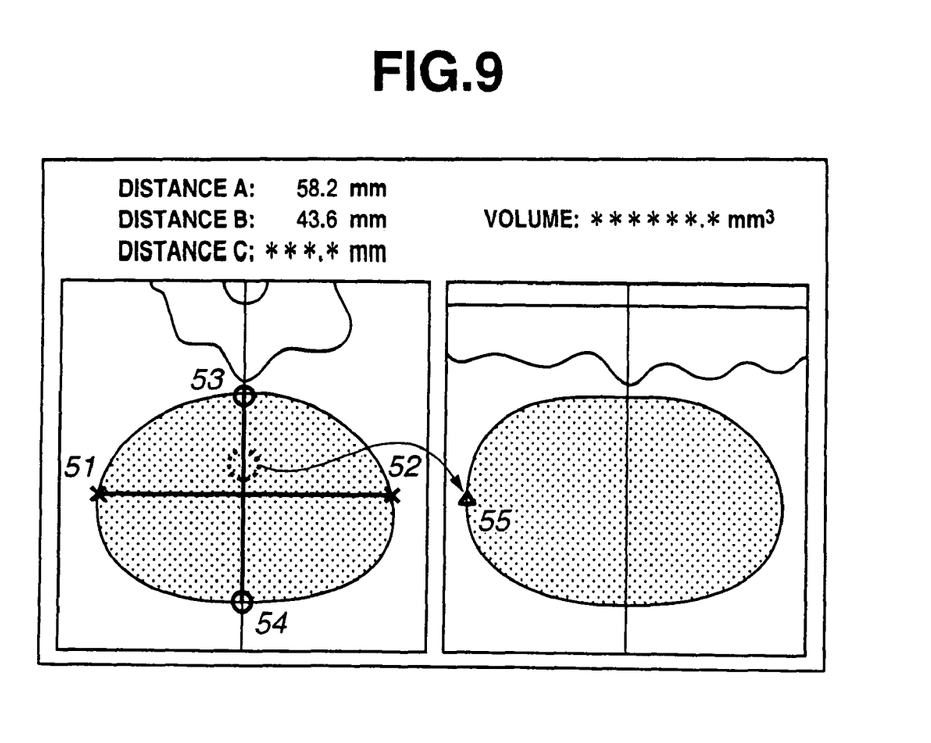
FIG. 9 is a sixth illustration showing a step for measuring the volume of the specific tissue shown in FIG. 3.
Figure 10:
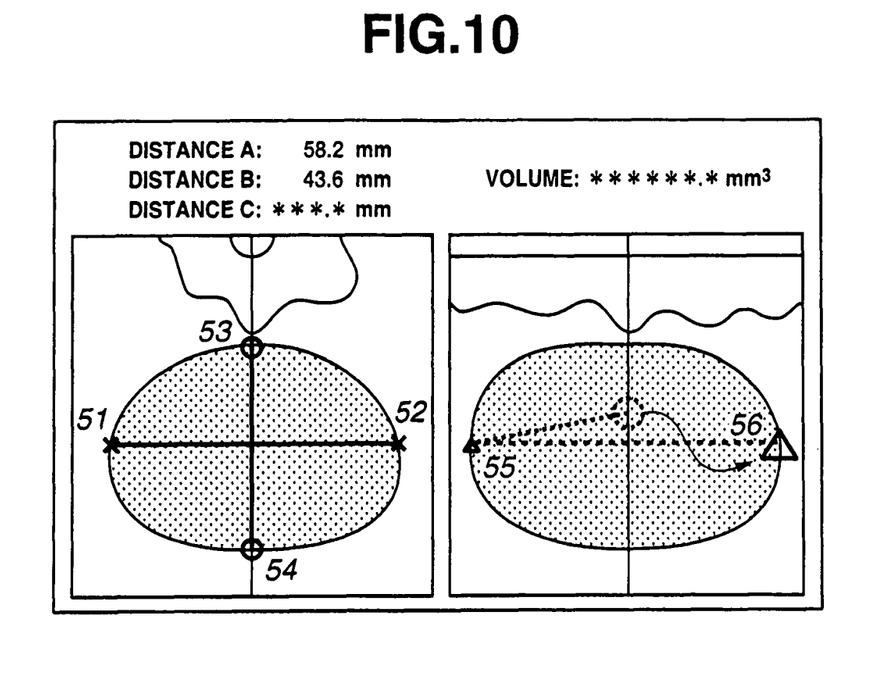
FIG. 10 is a seventh illustration showing a step for measuring the volume of the specific tissue shown in FIG. 3.
Figure 11:
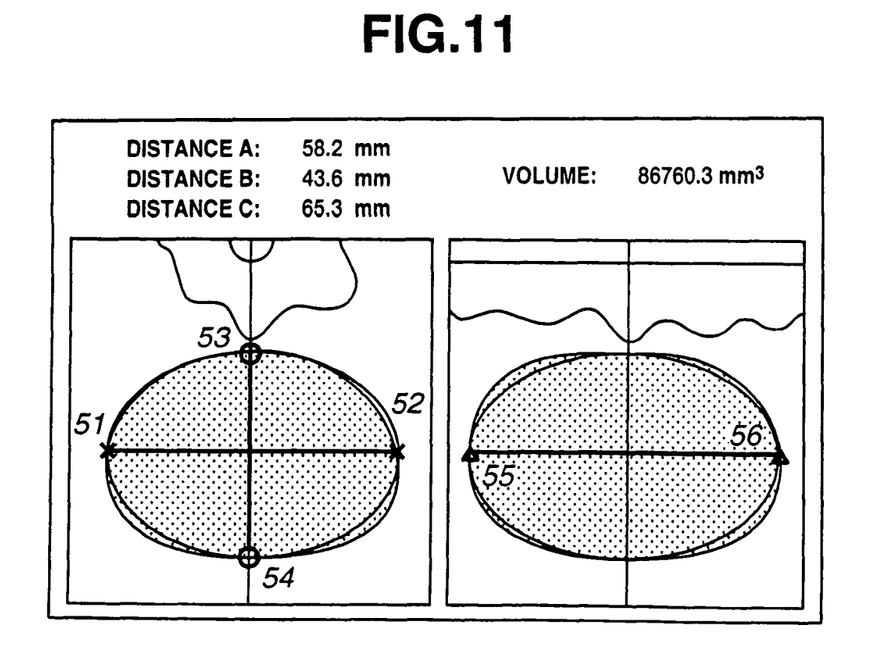
FIG. 11 is an eighth illustration showing a step for measuring the volume of the specific tissue shown in FIG. 3.
Figure 12:
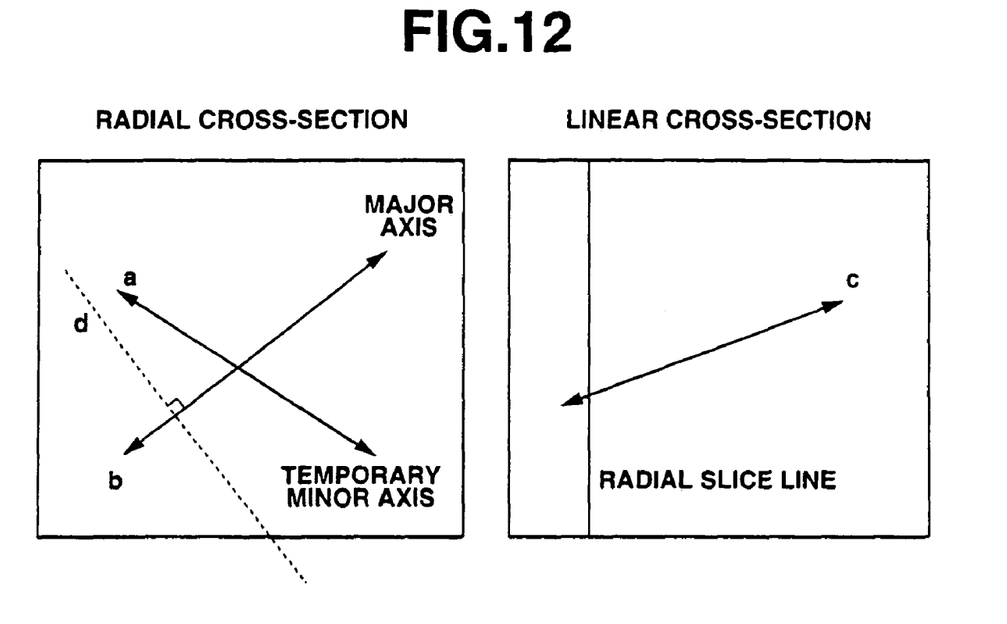
FIG. 12 is a first illustration showing calculation for the volume measurement according to the steps shown in FIGS. 4 through 11.
Figure 13:
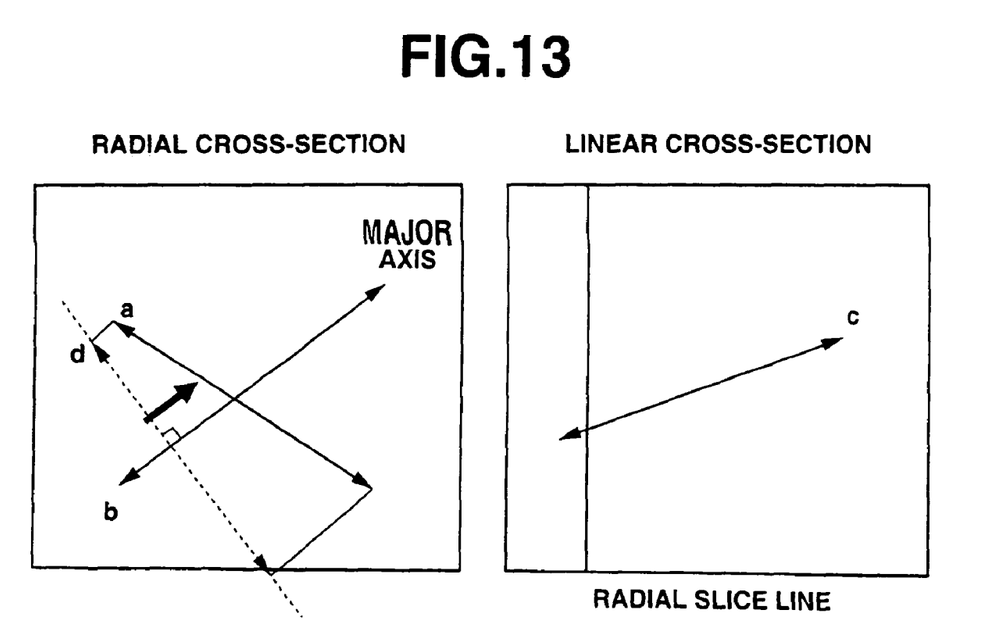
FIG. 13 is a second illustration showing calculation for the volume measurement according to the steps shown in FIGS. 4 through 11.
Figure 14:
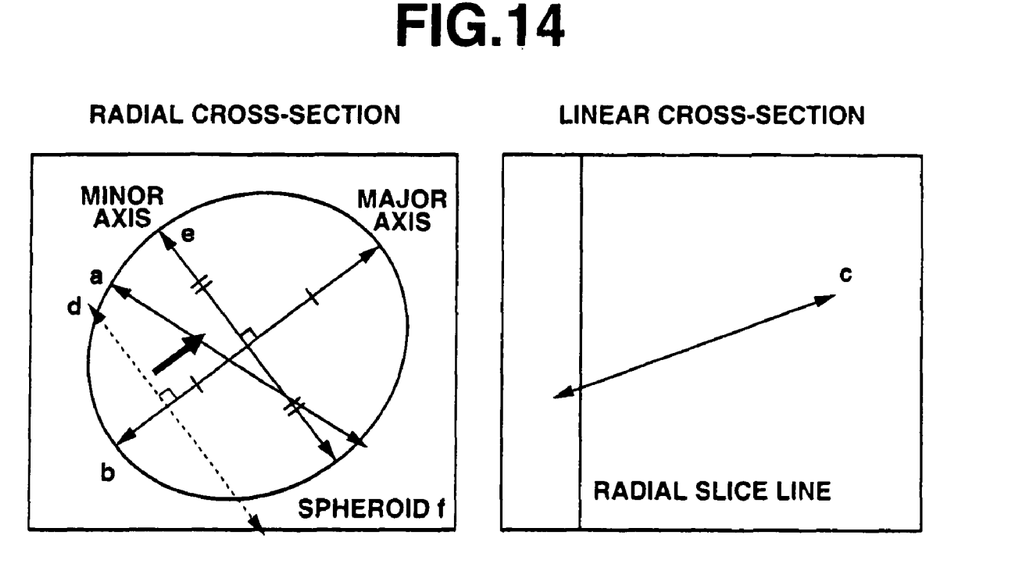
FIG. 14 is a third illustration showing calculation for the volume measurement according to the steps shown in FIGS. 4 through 11.
Figure 15:
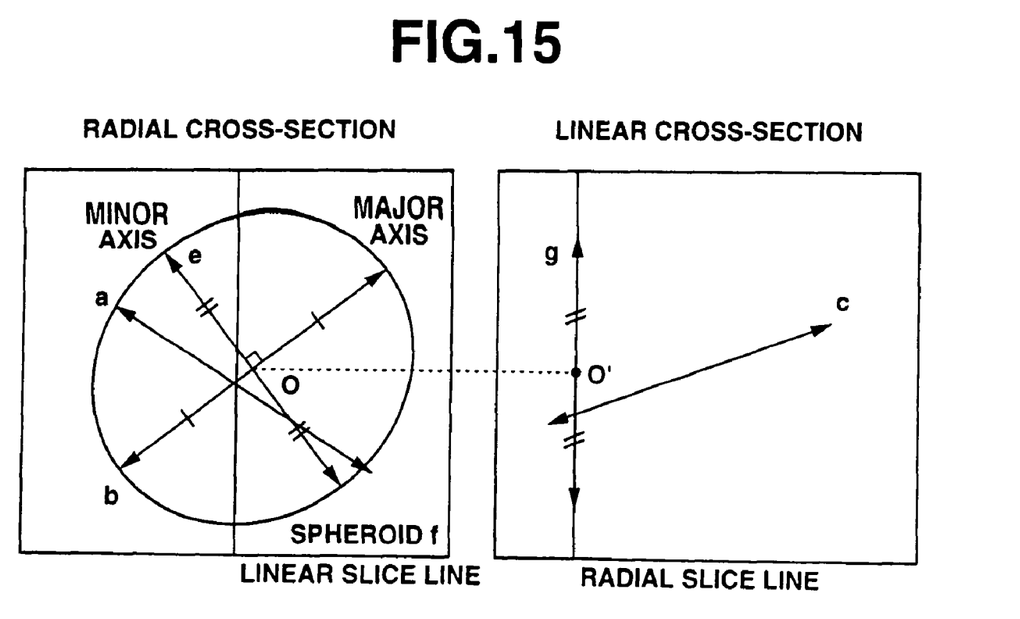
FIG. 15 is a fourth illustration showing calculation for the volume measurement according to the steps shown in FIGS. 4 through 11.
Figure 16:
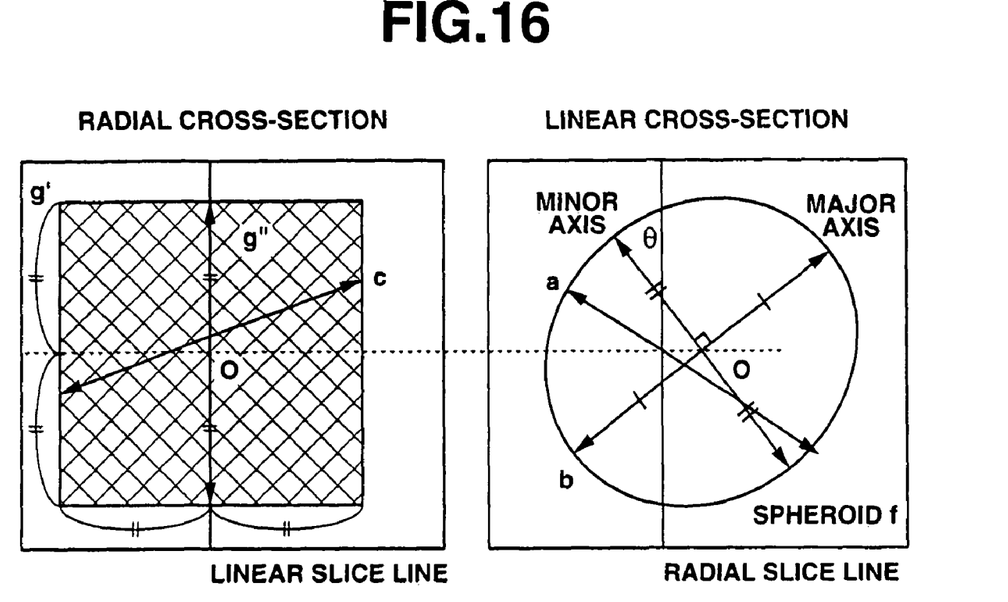
FIG. 16 is a fifth illustration showing calculation for the volume measurement according to the steps shown in FIGS. 4 through 11.
Figure 17:
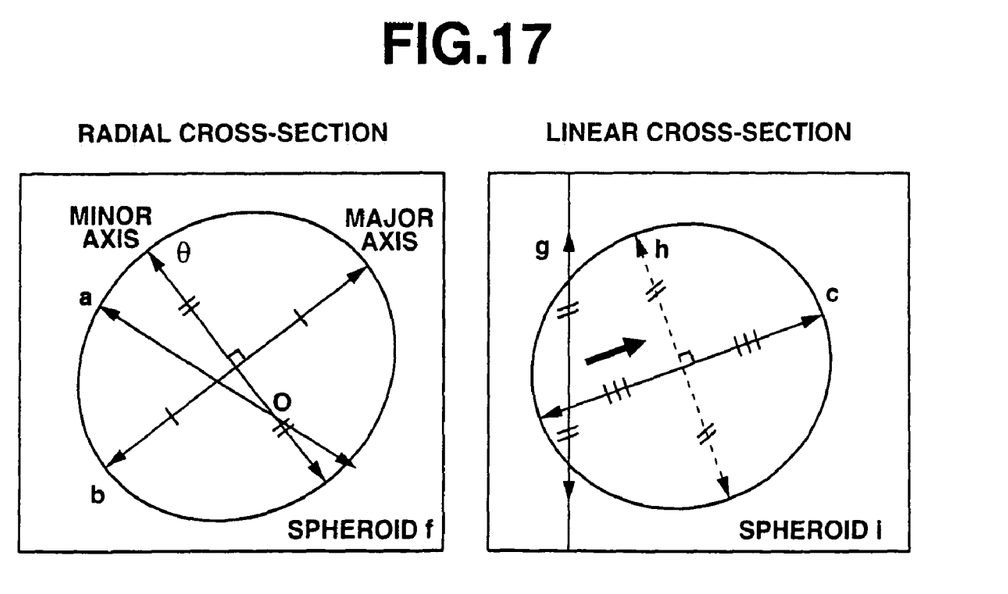
FIG. 17 is a sixth illustration showing calculation for the volume measurement according to the steps shown in FIGS. 4 through 11.

FIGS. 1 through 17 relate to a first embodiment of the present invention. FIG. 1 is a block diagram showing an ultrasonic image diagnostic apparatus. FIG. 2 is an illustration showing images (images in which a radial cross-section and a linear cross-section are developed) which are processed by an image processing circuit based on three-dimensional echo data stored in a memory shown in FIG. 1. FIG. 3 is an illustration showing a specific tissue (for instance, the prostate) in a lower semicircle display (display showing only the lower half from the center) of the radial cross-section shown in FIG. 2. FIG. 4 is a first illustration showing a step for measuring the volume of the specific tissue shown in FIG. 3. FIG. 5 is a second illustration showing a step for measuring the volume of the specific tissue shown in FIG. 3. FIG. 6 is a third illustration showing a step for measuring the volume of the specific tissue shown in FIG. 3. FIG. 7 is a fourth illustration showing a step for measuring the volume of the specific tissue shown in FIG. 3. FIG. 8 is a fifth illustration showing a step for measuring the volume of the specific tissue shown in FIG. 3. FIG. 9 is a sixth illustration showing a step for measuring the volume of the specific tissue shown in FIG. 3. FIG. 10 is a seventh illustration showing a step for measuring the volume of the specific tissue shown in FIG. 3. FIG. 11 is an eighth illustration showing a step for measuring the volume of the specific tissue shown in FIG. 3. FIG. 12 is a first illustration showing calculation for the volume measurement according to the steps shown in FIGS. 4 through 11. FIG. 13 is a second illustration showing calculation for the volume measurement according to the steps shown in FIGS. 4 through 11. FIG. 14 is a third illustration showing calculation for the volume measurement according to the steps shown in FIGS. 4 through 11. FIG. 15 is a fourth illustration showing calculation for the volume measurement according to the steps shown in FIGS. 4 through 11. FIG. 16 is a fifth illustration showing calculation for the volume measurement according to the steps shown in FIGS. 4 through 11. FIG. 17 is a sixth illustration showing calculation for the volume measurement according to the steps shown in FIGS. 4 through 11.

As shown in FIG. 1, an ultrasonic image diagnostic apparatus 100 according to the present embodiment includes an ultrasonic three-dimensional probe (hereinafter, referred to as an ultrasonic 3D probe) 1 that has an ultrasonic oscillator 15 (see FIG. 2) disposed at a tip end of an inserting portion (not shown), and is capable of acquiring three-dimensional echo signals (analog signals) through transmission and reception of ultrasonic waves by using the ultrasonic oscillator 15 according to a drive transmitting/receiving unit 1a; an image processor 2 that has later-described measurement line setting means and measurement means for performing various image processing based on the three-dimensional echo data acquired by the ultrasonic 3D probe 1; a monitor 3 that is display means for displaying the images that have already been image processed by the image processor 2; and an input unit 4 (keyboard, mouse, trackball, or the like) that allows operation, instruction, and the like, to be input.

The ultrasonic 3D probe 1 is inserted by an operator (doctor or the like) into a body of an examinee, for instance, a luminal organ, such as the stomach, esophagus, or large intestine. Then, the ultrasonic oscillator 15, for instance, provided at the tip end, is driven and rotated by the drive transmitting/receiving unit 1a, for performing radial scanning by rotating the ultrasonic oscillator 15, linear scanning by advancing or retracting the ultrasonic oscillator 15 in the longitudinal direction, or spiral scanning according to the combination of the radial scanning and the linear scanning. Upon the scanning, the ultrasonic 3D probe 1 transmits and receives the ultrasonic waves, acquires the three-dimensional echo of the luminal organ, and transmits the three-dimensional echo as three-dimensional echo signals, which are electric analog signals, to the image processor 2.

The image processor 2 includes a signal processing circuit 6 that performs signal processing such as envelope detection, logarithmic amplification, analog-digital conversion, scan conversion, or the like, for the three-dimensional echo signals transmitted from the ultrasonic 3D probe 1 to be converted into three-dimensional echo data (digital data), and constitutes a part of the measurement line setting means; a memory 7 that stores at least one set of plural sets of three-dimensional echo data converted by the signal processing circuit 6; a large capacity storage unit 8; a control circuit 9 that controls input and output signals of the input unit 4; an image processing circuit 10 that performs image processing such as coordinate conversion based on the three-dimensional echo data stored in the memory 7 and constitutes a part of the measurement line setting means for constructing developments of the cross sections as shown in FIG. 2; a display circuit 11 that converts the ultrasonic three-dimensional images processed by the image processing circuit 10 into video signals so as to be displayed on the monitor 3; a CPU 12 that controls the memory 7, the storage unit 8, and the circuits 6, 9, 10 and 11, and has the measurement means being stored for performing calculation of later-described "volume measurement"; and a data transmission bus (hereinafter, referred to as bus) 13 that connects each of the sections, i.e., the CPU 12, the memory 7, the storage unit 8, and the circuits 6, 9, 10 and 11, and allows the sections to transmit or receive the image data or the like.

FIG. 2 is an illustration showing images which are processed by the image processing circuit 10 based on the three-dimensional echo data stored in the memory 7, and shows a DPR (Dual Plane Reconstruction) display in which a first cross-section (radial cross-section) perpendicular to the longitudinal axis direction of the ultrasonic 3D probe 1, and a second cross-section (linear cross-section) parallel to the longitudinal axis direction of the ultrasonic 3D probe 1, are developed.

FIG. 3 is an illustration showing a specific tissue (for instance, the prostate) in a lower semicircle display (display showing only the lower half from the center) of the radial cross-section in the DPR display. A dotted area (hatching area) having numerical reference 16 shown in FIG. 3 is the specific tissue.

Then, steps for measuring the volume of the specific tissue 16 shown in FIG. 3 by the operator, will be described with reference to FIGS. 4 through 11.

The operator gives the instruction of the measurement by using the input unit 4 while the shape of the specific tissue 16 is displayed on the monitor 3 in the first and second cross-sections. Accordingly, the image processing circuit 10 constructs an ultrasonic three-dimensional image for specific tissue measurement (hereinafter, referred to as measurement image) shown in FIG. 4 for measuring the specific tissue 16 based on the three-dimensional echo data stored in the memory 7 in response to the input instruction, and displays the measurement image on the monitor 3 via the display circuit 11.

Then, when recognizing the specific tissue 16 in the measurement image, the operator selects "distance measurement" from measurement items and determines it by using the input unit 4.

Upon the determination, the CPU 12 displays a caliper 51 to be superimposed at the center of the first cross-section image in the measurement image as shown in FIG. 4.

When the caliper 51 is moved to an end of the specific tissue 16 by using the input unit 4 (see FIG. 5) and is set, an active caliper 52, the shape of which is the same as that of the caliper 51, appears at the center of the first cross-section image. At the same time, the size of the position-set caliper 51 becomes one size smaller than the original size, so that the caliper 51 is distinguishable from the active caliper 52. Then, the caliper 52 is moved to another end of the specific tissue 16 substantially opposite to the caliper 51 (FIG. 6) and is set, and accordingly, the distance of a segment x defined between the calipers 51 and 52 is displayed.

Then, when the operator newly selects "distance measurement" of a second system by using the input unit 4, a caliper 53, the shape of which is different from that of the caliper of the first system, appears at the center of the first cross-section image. The caliper 53 is moved by the operator to the vicinity of an end, at which a line passing through the midpoint of the segment x and perpendicular to the segment x intersects with the border of the specific tissue 16 (FIG. 7), and the caliper 53 is set. At the same time, an active caliper 54, the shape of which is the same as that of the caliper 53, appears at the center of the first cross-section image. Then, the caliper 54 is moved to another end of the specific tissue 16 (FIG. 8) in the same manner as that of the segment x, and is set. Accordingly, the distance of a segment y is displayed.

Then, when the operator newly selects "distance measurement" of a third system by using the input unit 4, a caliper 55, the shape of which is different from that of the calipers of the first system and the second system, appears at the center of the first cross-section image. The caliper 55 is moved by the operator operating an input circuit 4 to the vicinity of an end, which intersects with the border of the specific tissue 16 in the second cross-section image (FIG. 9), and the caliper 55 is set. At the same time, an active caliper 56, the shape of which is the same as that of the caliper 55, appears at the center of the second cross-section image. Then, the caliper 56 is moved to another end of the specific tissue 16 (FIG. 10), and is set. Accordingly, the distance of a segment z is displayed, and the result of volume measurement (spheroidal approximation) is displayed (FIG. 11).

Next, calculation of the above-described volume measurement will be described below with reference to FIGS. 12 through 17.

(1) In the first cross-section (radial cross-section) with the two systems being input, a system corresponding to a long distance is assumed as a major axis (in this case, assumed as measurement segment b), and another system is assumed as a temporary minor axis. Then, a line d perpendicular to the major axis is considered (see FIG. 12).

(2) The temporary minor axis is projected to the line d perpendicular to the major axis, and the length of the minor axis is determined (see FIG. 13).

(3) A minor axis e, which is a perpendicular bisector of the major axis and is determined according to (2), is determined. Then a spheroid f, which is circumscribed to the determined major axis b and minor axis e, is determined (see FIG. 14).

(4) A segment g is considered. The segment g has a length corresponding to the minor axis e centered at O' on a radial slice line in the linear cross-section, O' being a height position of an intersection point O at which the major axis b and minor axis e of the spheroid f intersect with each other (see FIG. 15, in a case of the input with two systems applied to the linear cross-section, and one system applied to the radial cross-section, a rectangular region g' is considered, the region g' having the height of the center position corresponding to the intersection point O and the width in the height direction thereof corresponding to the length of the minor axis).

(5) If the segment g intersects with the measurement segment c [or if the region g' (its width in the height direction being equivalent to the minor axis, the height of the center O' being equivalent to that of the center O, the center in the lateral direction being coincide with that of the linear slice line, and the width being equivalent to the minor axis) includes an end point of the measurement segment c and the measurement segment c intersects with a segment g" on the linear slice line], these segments g and c become the subject of the spheroid measurement (see FIG. 16).

(6) The measurement segment c and a third axis h are considered, the third axis h perpendicularly bisecting the measurement segment c while being perpendicularly bisected by the measurement segment c, and having a length equivalent to that of the minor axis. Then, a spheroid i having the measurement segment c and the third axis h as the axes thereof is considered (see FIG. 17).

(7) The calculation is performed by applying the length of each axis into the following equation for calculating a volume estimation V:

$$V=(4\pi/3)\times(a'/2)\times(b'/2)\times(c'/2)$$

where a' is the length of the major axis, b' is the length of the minor axis, and c' is the length of the measurement segment c, and the result of the calculation is displayed.

(8) The spheroid f and the spheroid i are displayed on the screen as ellipsoid displaying.

Note that when displaying the ellipsoid, all the following conditions (a) and (b) must be further satisfied.

(a) In a case where two systems are applied to the radial cross-section, and one system is applied to the linear cross-section:
One of the minor axis and the major axis intersects with a helical slice line, and
The system in the linear cross-section intersects with the radial slice line.

(b) In a case where two systems are applied to the linear cross-section, and one system is applied to the radial cross-section:
One of the minor axis and the major axis intersects with the radial slice line.

According to the above-described embodiment, advantages 1) through 4) can be attained.

1) Since a measurement range may be specified in the three-dimensional image, the measurement can be performed easily and accurately.

2) Since the volume measurement may be performed in a similar way to the distance measurement, operationality is not complicated.

3) The volume measurement can be performed while the distance measurement is performed.

4) The measurement range is visually recognizable since the volume measurement range is displayed.

It should be noted that the present invention is not limited to the above-described embodiment, and may be modified, improved, and the like, within the scope of the present invention.

What is claimed is:

1. An ultrasonic image diagnostic apparatus capable of performing three-dimensional ultrasonic scanning on a subject, and displaying an arbitrary first tomographic image of the subject and a second tomographic image perpendicular to a cross section of the first tomographic image, by using ultrasonic data in a three-dimensional region obtained according to the ultrasonic scanning, comprising:
an image processor, including a CPU, configured to:
set a first line segment and a second line segment, which are not parallel to each other, on the first tomographic image, and setting a third line segment, which is not parallel to the cross section of the first tomographic image, on the second tomographic image, as line segments to be measured;
set a longer line segment of the first and second line segments as a major axis, setting a line segment which is obtained by projecting a shorter line segment of the first and second line segments on an axis orthogonal to the major axis as a minor axis;
set the third line segment as a depth length; and
cause the CPU to perform a volume measurement of the subject by means of ellipsoidal approximation using only the first tomographic image and the second tomographic image in which the major axis, the minor axis, and the depth length are used as coefficients; and
a display configured to display a measurement result and a measurement range obtained by the image processor.

2. The ultrasonic image diagnostic apparatus according to claim 1, wherein a volume V of the subject is calculated from the following equation, $V=(4\pi/3)\times(a'/2)\times(b'/2)\times(c'/2)$ where a' is a length of the major axis, b' is a length of the minor axis, and c' is a length of depth (measurement segment), by means of the ellipsoidal approximation using the major axis, the minor axis, and the depth length as coefficients.

* * * * *